United States Patent [19]

Shaw, IV

[11] 4,039,836

[45] Aug. 2, 1977

[54] METHOD AND APPARATUS FOR BODY X-RAYING

[76] Inventor: Alexander F. Shaw, IV, 46 Gunning Point Road, Falmouth, Mass. 02540

[21] Appl. No.: 664,724

[22] Filed: Mar. 8, 1976

[51] Int. Cl.² ............................................. G03B 41/16
[52] U.S. Cl. ................................ 250/445 R; 250/322; 250/402; 250/452; 250/490; 250/525
[58] Field of Search ............... 250/439 R, 444, 445 R, 250/445 T, 446, 447, 448, 449, 450, 451, 452, 523, 524, 525, 490, 401, 402, 322

[56] References Cited

U.S. PATENT DOCUMENTS

| 2,078,340 | 4/1937 | Powers | 250/490 |
| 3,150,260 | 9/1964 | Smith | 250/450 |
| 3,492,482 | 1/1970 | Forsyth | 250/525 |

*Primary Examiner*—Craig E. Church
*Attorney, Agent, or Firm*—Henderson, Strom & Sturm

[57] ABSTRACT

An apparatus for X-raying having a source structure for providing X-rays. A patient is disposed in front of a bucky having a grid and film cassette. A support structure is disposed at a distance from the bucky and parallel thereto, the patient being therebetween. The source structure for the X-rays is attached to the support structure and is slidable along the length thereof. A motor moves the source structure at variable rates of speed along the length of the support structure. A feedback mechanism is attached to the source structure, moving therewith along the length of the support structure, and also is coupled to the motor. The feedback mechanism detects the thickness of the body areas of the patient through which X-rays are passing or the quantity of X-rays passing completely therethrough, and adjusts the motor speed such that the duration of exposure to X-rays of the patient's body area in the vertical dimension is directly proportional to the thickness of each area or inversely proportional to the quantity of X-rays passing therethrough.

12 Claims, 11 Drawing Figures

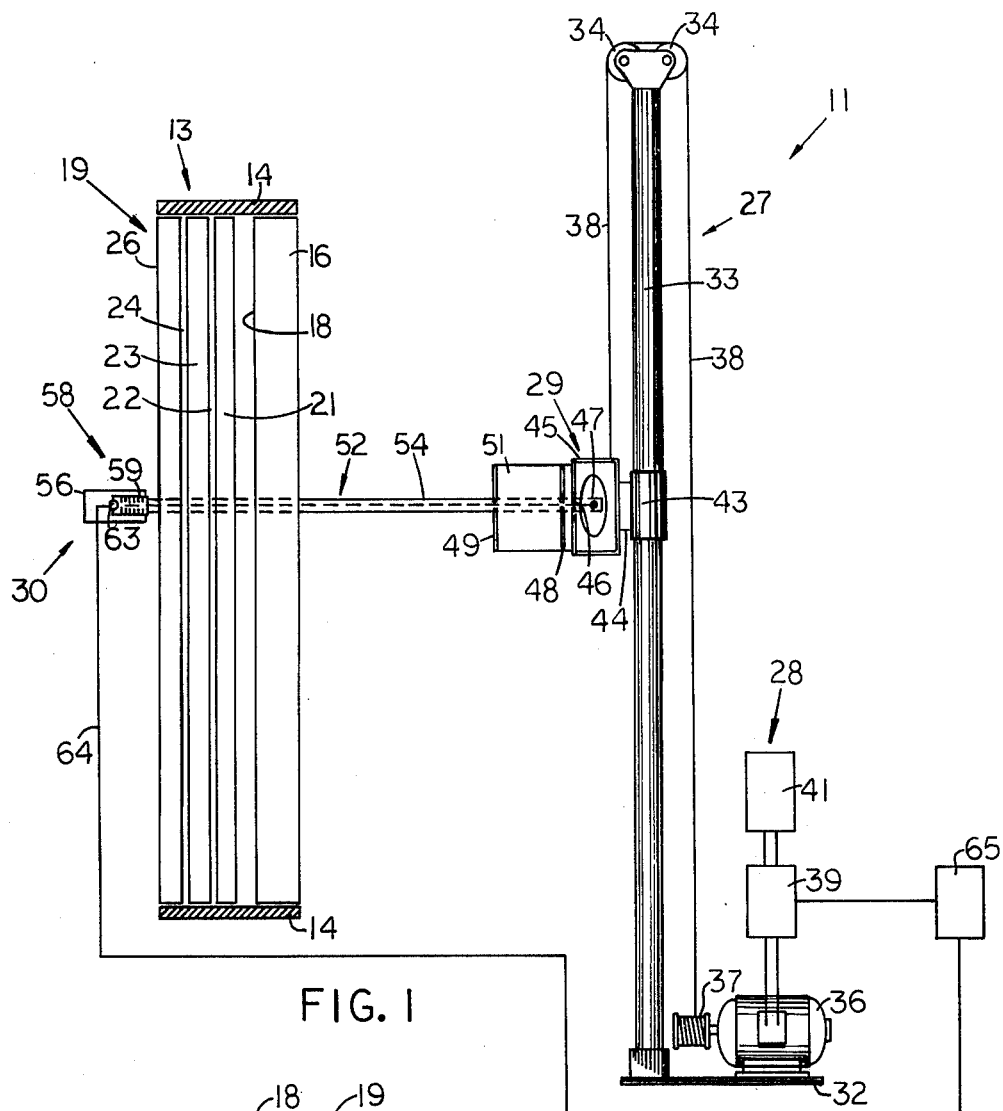
FIG. 1
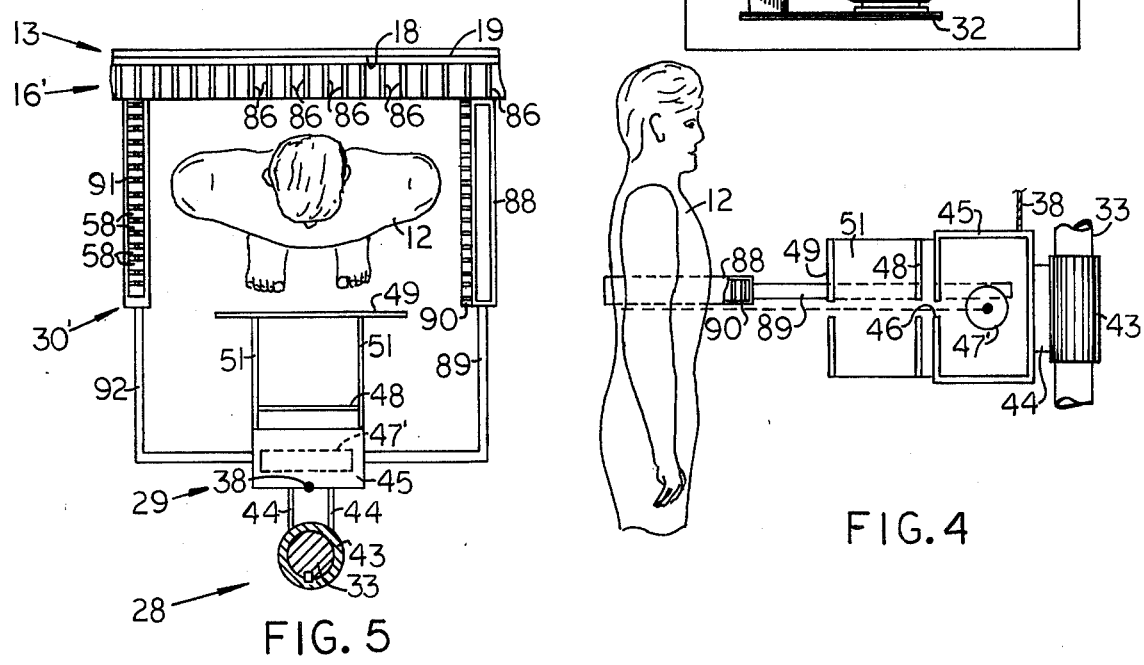
FIG. 5
FIG. 4

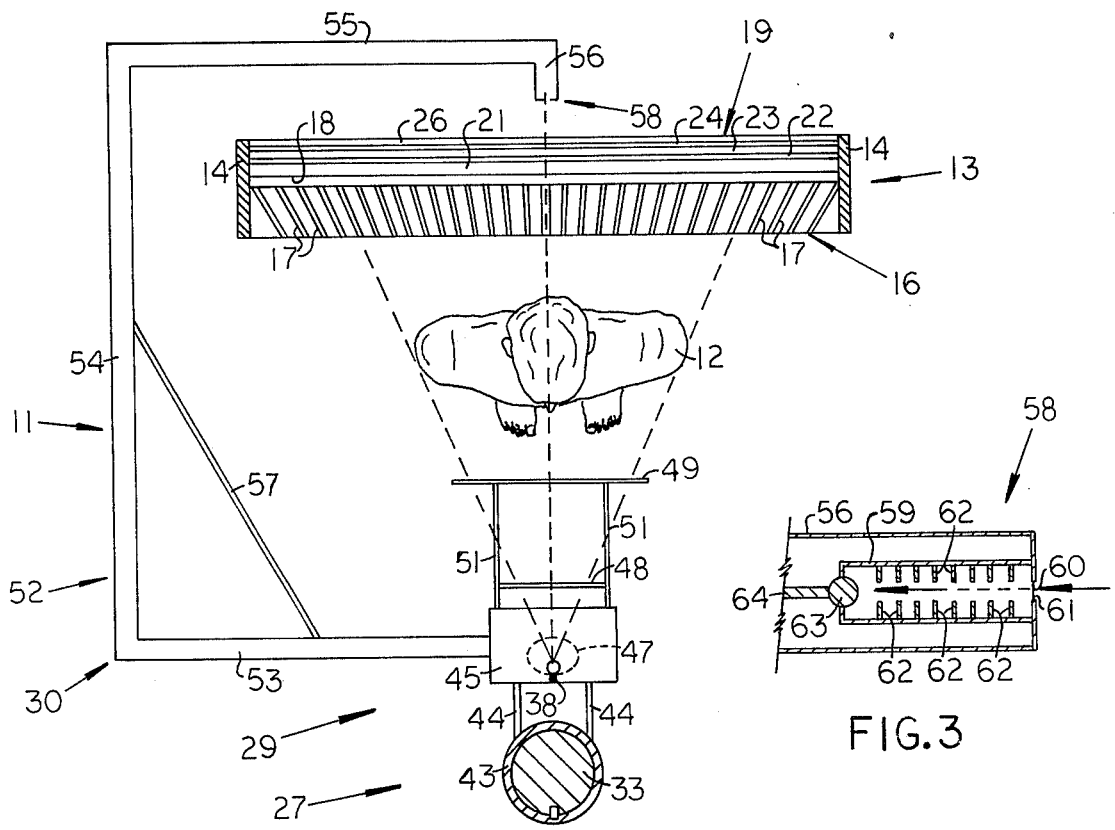
FIG. 2
FIG. 3
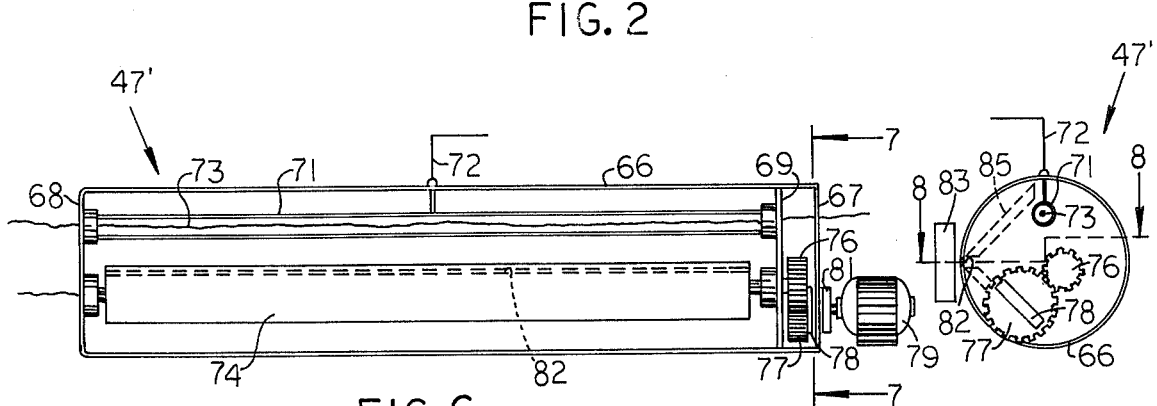
FIG. 6
FIG. 7
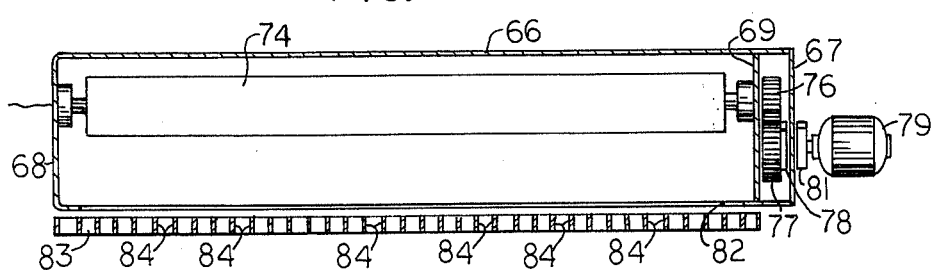
FIG. 8

METHOD AND APPARATUS FOR BODY X-RAYING

BACKGROUND OF THE INVENTION

This invention relates generally to medical X-ray apparatus, particularly to X-ray apparatus having chiropractic applications, such as full body or full spine analysis of a patient. Conventionally, a patient stands in front of a bucky, and an X-ray tube is mounted several feet, most commonly about 6 feet (183 cm), therefrom. The X-ray beam spreads in all directions sufficiently to pass through all areas of the patient's body. A somewhat phosphorescent screen contained in the bucky produces an image of the patient which is captured on the film.

A number of deficiencies are inherent in the current methods of X-raying. The X-ray tube must be placed at a substantial distance from the patient, and therefore there are large power requirements such that a beam of adequate intensity to expose the film in the bucky is obtained. Additionally, all body areas of the patient currently receive the same exposure to the X-rays. To adequately expose the lumbar area of the patient, the thoracic area is exposed more than is necessary, and the cervical region is over-exposed. The patient generally is exposed to more radiation than is desirable.

A further deficiency in the current methods of body X-raying arises from the diversion of the X-ray beam, such that some parts of the body cannot be seen at precisely right angles to determine their exact measurements and relationships over all parts of the film. X-rays along the axis of the cone of the X-ray beam pass through the patient to strike the film in the bucky perpendicularly. All other X-rays pass through the patient at angles diverging from the axis of the cone to strike the film at an oblique angle. The image of the body parts upon the film therefore is distorted and not linearly proportioned, and the exact angles and relationships between parts of the body are difficult to determine.

Intensifiers in the form of phosphorescent screens have been inserted into the bucky on each side of the film to produce better film quality. These screens are activated by X-rays passing therethrough and aid in exposing the film. A plurality of screens, each having different speeds, have been inserted into the bucky behind the different body areas of the patient. Nevertheless, the aforementioned disadvantages have not been overcome.

SUMMARY OF THE INVENTION

An apparatus for X-raying a patient is disposed in front of a bucky and has an upstanding support member which is disposed parallel to the bucky, the patient being disposed between the bucky and the support member. An X-ray source is mounted within a housing, which housing is attached to the support member and slidable along the length thereof. Collimator structures are attached to the housing and travel therewith along the length of the support member. A motor moves the housing along the length of the support member. A feedback structure is attached to the housing and detects the thickness of different areas of the body of the patient or the quantity of X-rays passing therethrough. The feedback structure is connected to the motor and alters the speed of the motor, thereby changing the rate of movement of the housing along the support member in inverse proportion to the thickness of the body area being exposed to X-rays or in direct proportion to the quantity of X-rays passing therethrough. The collimator structures ensure that a thin, horizontal beam, rather than a cone, of X-rays is directed toward the patient. An image is formed upon the film held within the cassette of the bucky, which image is used for analysis of the condition of the patient.

An object of this invention is to provide an X-ray apparatus which will provide X-ray films which are sharp and free of magnification and which therefore will greatly facilitate analysis of the condition of patients.

Another object of this invention is to provide an X-ray apparatus which ensures maximum safety to the patient being X-rayed by reducing the amount of exposure of the patient to radiation.

It is a further object of this invention to provide an X-ray apparatus which will reduce the energy requirements of taking X-ray films for analysis of patients.

These objects and other features and advantages of the X-ray apparatus of this invention will become readily apparent upon referring to the following description, when taken in conjunction with the appended drawings.

BRIEF DESCRIPTION OF THE DRAWING

The X-ray apparatus of this invention is illustrated in the drawing wherein:

FIG. 1 is a side elevational view of the first embodiment of the X-ray apparatus, parts of the feedback mechanism being enlarged and shown in longitudinal section and in schematic for greater clarity, the bucky being enlarged and shown in section for greater clarity, and portion of the collimator structures and housing being shown in section for greater clarity;

FIG. 2 is an enlarged top plan view of the first embodiment of the X-ray apparatus, parts of the support structure being cut away and the bucky being further enlarged and shown in sectional view for greater clarity;

FIG. 3 is an enlarged, fragmentary longitudinal sectional view of the photocell detector structure shown in FIG. 1;

FIG. 4 is a fragmentary, side elevational view of the second embodiment of the X-ray apparatus;

FIG. 5 is a fragmentary, top plan view of the second embodiment, the bucky being enlarged and portions of the frame thereof being cut away for greater clarity;

FIG. 6 is an end elevational view of the first extended X-ray source of this invention, the grid being cut away to show the internal mechanism of the X-ray source;

FIG. 7 is a cross sectional view taken along line 7—7 in FIG. 6;

FIG. 8 is a hoizontal sectional view taken along line 8—8 in FIG. 7;

DESCRIPTION OF THE PREFERRED EMBODIMENT

Figure 9:
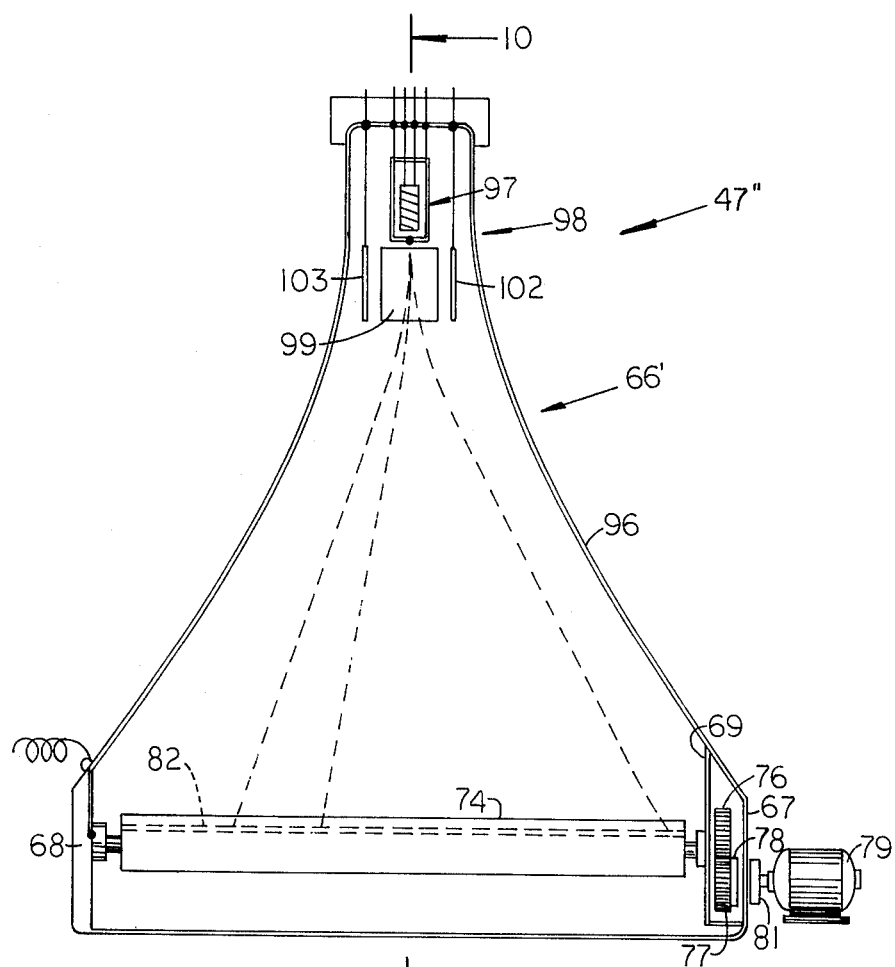
FIG. 9 is a front elevational view of the second extended X-ray source of this invention.

Referring now to the drawings, the first embodiment of the invention is indicated generally at 11 in FIGS. 1 and 2. A patient 12 (FIG. 2) is disposed between the X-ray apparatus 11 of this invention and a bucky 13 in preparation for the taking of X-ray photographs. The invention 11 more particularly includes a support mechanism 27, motor mechanism 28, X-ray source mechanism 29 and feedback mechanism 30.

The standard bucky 13 illustrated in FIGS. 1 and 2 is normally of a thickness approximately equal to the width of the ears of the patient 12, but is herein illustrated enlarged out of scale for greater clarity. The bucky 13 includes a rectangular frame member 14. A grid member 16 comprised of a plurality of lead plates 17 is disposed within the frame 14 toward the side of the bucky 13 facing the patient 12. The lead plates 17 may either be movable or reciprocating, or the plates 17 may be preset at given angles with respect to the source 29 such that the planes defined by the individual plates 17 intersect at the source 29. A small space 18 separates a cassette 19 from the grid 16. The cassette 19 is disposed within the frame 14 to the rear thereof and in parallel with the grid 16. The cassette 19 includes a plastic sheet member 21, a high speed phosphorescent screen 22, a film member 23, a second high speed phosphorescent screen 24 and a sheet 26, made of lead or other suitable material. The members 21, 22, 23, 24, 26 abut, the plastic sheet 21 facing toward the grid 16, the sheet 26 facing to the rear of the bucky 13, and the screens 22, 24 and film 23 being located between the sheets 21, 26. The screens 22, 24 separate the film 23 from the sheets 21, 26.

The first embodiment of the X-ray apparatus of this invention 11 is depicted in FIGS. 1, 2 and 3. The support mechanism 27 includes a flat base member 32 which engages the ground or floor. A vertically disposed cylindrical support 33 extends upwardly from the base 32. Pulleys 34 are attached to the upper end of support 33.

The motor mechanism 28 (FIG. 1) includes a motor 36 attached to the base 32. The shaft of the motor 36 bears a reel 37. A lift wire or cable 38 is wound upon the reel 37 and extends upwardly therefrom adjacent one side of the support 33, to pass over the pulleys 34. A control circuit 39 is interposed in the circuit between the motor 36 and the motor power supply 41.

The X-ray source mechanism 29 (FIGS. 1 and 2) includes a gliding suport having a sleeve 43 and plates 44. The sleeve 43 is elongated and annular in cross-section, and the sleeve 43 fits over the vertical support 33 and is slidable along the length thereof. Two parallel and vertically disposed support plates 44 are affixed to the sleeve 43. A box-like housing 45, within which the X-ray tube or source 47 is arranged, is attached to the ends of the plates 44, and the cable 38 is attached to the housing 45. The front side of the housing 45 has a horizontally disposed slit 46 formed therein. First amd second collimator plates 48, 49 are connected by two support plates 51 to the front side of the housing 45. The first collimator plate 48 is disposed adjacent the front of the housing 45, and the second collimator plate 49 is disposed adjacent the patient 12. The horizontal slits of the plates 48, 49 and the slit 46 of the housing 45 are aligned in a horizontal plane, which plane is perpendicular to the patient 12 and to the bucky 13.

The feedback mechanism 30 (FIGS. 1 and 2) includes a holder bar 52. The holder bar 52 is attached to the housing 45 and extends therefrom to terminate at a position behind the bucky 13. The holder bar 52 may be attached to either side of the housing 45 and is therefore illustrated extending from the right side of the housing 45 in FIG. 1 and the left side thereof in FIG. 2. The holder bar 52 is disposed in the horizontal plane defined by the slits of the collimators 48, 49 and the slit 46. A first portion 53 is attached to the housing 45 and extends therefrom parallel to the plates 48, 49. A second portion 54 is attached normal to portion 53 and extends therefrom beyond the bucky 13. A third portion 55 is attached perpencidular to the portion 54 and extends therefrom parallel to and behind the bucky 13. A short fourth portion 56 is affixed normal to the portion 55 and extends toward the bucky 13. A support or brace 57 extends between the first and second portions 53, 54 of the holder bar 52. A photocell detector structure 58 is supported within the portion 56 at the end of the holder bar 52.

The photocell detector structure 58 (FIG. 3) includes an elongated cylindrical clarifier member 59 which is attached normal to the end wall of the portion 56 and directly over an aperture 60 formed therethrough. A thin sheet 61 which is opaque to visible light is stretched over the aperture 60. A plurality of lead washers or baffles 62 are attached to the inside of the member 59. The baffles 62 are annular in shape and are uniformly spaced and disposed parallel to ach other and to the end wall of the portion 56. A photocell 63 coated with a somewhat phosphorescent material is attached in the end of the member 59 opposite the aperture 60. A conductor 64 leads therefrom to a detection circuit 65 (FIG. 1), which circuit 65 is connected to the control circuit 39. A straight line between the X-ray source 47 and the photocell 63 is perpendicular to the bucky 13 and the plates 48, 49 and is disposed within the horizontal plane defined by the slit 46 and the slits of the collimators 48, 49, passing therethrough and through the aperture 60 and the central apertures of the annular shaped baffles 62.

The second and preferred embodiment of the X-ray apparatus of this invention 11 is illustrated in FIGS. 4 through 11. A linear X-ray source 47' of the X-ray apparatus of the preferred embodiment of this invention 11 is shown in FIGS. 4–8. The source 47' includes an elongated, cylindrical glass tube 66 having first and second closed ends 67, 68. A support 69 is disposed within the tube 66, adjacent the first end 67 and parallel thereto. An elongated, cylindrical cathode 71 is attached between the second end 68 and support 69 and perpendicular thereto. The cathode 71 has at least one conductor 72 connected thereto and a filament wire 73 passing therethrough. The cathode 71 is positioned halfway between the central longitudinal axis of the tube 66 and the glass wall of the tube 66 and is within the upper half of the space enclosed by the tube 66. A longitudinal slit (not shown) may be formed in the underside of the cathode 71 such that a vertical plane bisecting the cathode 71 would pass therethrough.

The X-ray source 47' also includes an elongated, cylindrical anode 74. The anode 74 extends between the second end 68 and the support 69, being rotatably affixed thereto, and is disposed parallel to the cathode 71. The anode 74 is rotatable about its longiduinal axis, being directly connected to a small, driven gear 76 disposed on the opposite side of the support 69. A larger driving gear 77 is rotatably attached to the support 69 and meshes with the gear 76. An elongated magnetic member 78 is attached to the gear 77 along a diameter thereof and is adjacent to the end 67.

A motor 79, having a slow speed-up mechanism (not shown), is positoned external to the tube 66 adjacent the first end 67 thereof. The shaft of the motor 79 bears a magnetic member 81 which is disposed adjacent the end 67 and which is rotatable in a plane parallel to the end 67 and to the plane in which the member 78 rotates.

The tube 66 may be formed of a clear glass or other clear material entirely, or of a lead glass but with a clear glass over the focal line slit area 82 (FIGS. 6 and 7). Planes extending from the central longitudinal axis of the tube 66 and passing through the cathode 71 and through the slit area 82 enclose a quadrant of the interior space of the tube 66 (FIG. 7). The surface of the anode 74 is parallel to the central longitudinal axis of the tube 66 and passes therethrough when the anode 74 is rotated. The anode 74 is positioned within the tube 66 such that the vertical path between the cathode 71 and the central longitudinal axis of the tube 66 impinges upon the surface of the anode 74 with an angle of incidence of from 5° to 30°. The X-ray source 47' with its motor 79 are positioned within the housing 45 such that the area 82 is disposed within the horizontal plane defined by the slit 46 and the slits of the collimators 47, 48. A grid 83 having a plurality of parallel lead plates 84 is installed within the housing 45 adjacent the tube 66 and in front of the area 82. The plates 84 are vertically disposed and are perpendicular to the area 82. to the area 82. As shown in hatched lines in FIG. 7, lead plated 85 may be inserted within the tube 66.

Figure 10:
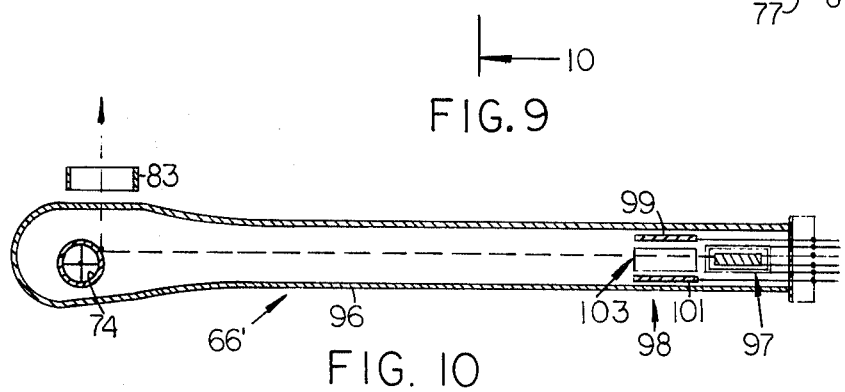
FIG. 10 is a transverse sectional view, taken along line 10—10 of FIG. 9.

A modified linear X-ray source 47" is depicted in FIGS. 9 and 10. The source 47" has a modified tube 66' with first and second ends 67, 68 and internal support 69, as described previously, but having a tapering elongated portion 96. The tube 66' is vertically disposed when the source 47" is secured within the housing 45 and has a somewhat triangular configuration when viewed from the front (FIG. 9). At the upper end of the tube 66' is located a cathode structure 97 and a beam control mechanism 98. The mechanism 98 includes front and rear adjustment plates 99, 101 and right and left sweep plates 102, 103 connected to appropriate circuitry (not shown). At the lower end of the tube 66' the anode 74 is disposed such that a vertical path from the cathode 97 has an angle of incidence thereupon of from 5° to 30°. The plates 99, 101, 102, 103 may be replaced by deflection electromagnets (not shown) attached to appropriate circuitry (not shown). Where deflection electromagnets (not shown) are used, an annular centering electromagnet (not shown) may be disposed about the tube 66' between the cathode structure 97 and the deflection electromagnets (not shown) and within a plane which is parallel to that plane within which the deflection electromagnets (not shown) are disposed. A cylindrical focusing anode (not shown) may be parallel to and longitudinally aligned with the cathode structure 97 and disposed between the cathode structure 97 and the annular centering electromagnet (not shown).

Figure 11:
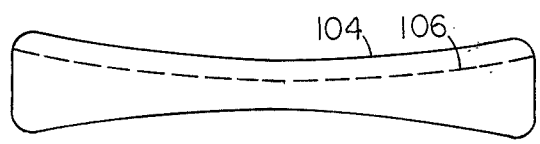
FIG. 11 is a front elevational view of a modified form of an anode for the second extended X-ray source of this invention.

FIG. 11 depicts a modified anode 104 which is somewhat saddle-shaped. Use of the anode 104 results in the length of the beam path between the cathode 97 and anode 104 remaining constant as the beam sweeps from end to end of the anode 104. Where the anode 104 is sued, the slit 46, and the slits in the plates 48, 49 are altered to an arcuate shape which conforms to that of the beam path, indicated at 106 in FIG. 11, over the anode 104 when the anode 104 is viewed in front elevation. The conformation of th plates 85 is also changed such that the space therebetween is similarly arcuate. The slit area 82 therefore also takes on an arcuate configuration.

As shown in FIGS. 4 and 5, the bucky 13 is used having a grid 16' with vertical plates 86 which are parallel with respect to each other and perpendicular to the cassette 19. A modified feedback mechanism 30' is used. An elongated light source 88 is attached by a support 89 to the housing 45, and an elongated light detector 91 is attached by a similar support 92 to the opposite side of the housing 45. The source 88 and detector 91 are disposed on opposite sides of the patient 12 and slightly above the horizontal plane defined by the slit 46 and the slits of the collimators 48, 49. A vertical grid 90 is attached to the source 88 on the side thereof facing the detector 91. The source 88 is depicted as being a flourescent light or other elongated light source. The source 88 may, however, be a plurality of discrete light sources (not shown) arranged in a side-by-side fashion along the length of the source 88 and directed toward the detector 91. The grid 90 would be replaced by a plurality of structures (not shown) similar in construction to clarifier structures 59, each associated with one of the discrete sources (not shown).

The light detector 91 depicted in FIGS. 4 and 5 has a plurality of photocell detector structures 58. The structures 58 are disposed in side-by-side fasion within the detector 91 and are directed toward the light source 88, the longitudinal axes of the structures 58 being parallel to the collimator plates 48, 49. Sheets 61 are not used to cover the apertures 60 formed in the light detector 91 for the photocell detector structures 58, and the photocells 63 employed do not have a phosphorescent coating and are responsive to wavelengths of the light source 88. The light detector 91 is connected to the detection circuit 65. The light detector 91 may alternately be a unitary, elongated light detecting structure (not shown) having a vertical grid (not shown) disposed adjacent thereto and toward the light source 88.

When the first embodiment of the X-ray apparatus of this invention 11 is used, the patient 12 is disposed as shown between the bucky 13 and the second collimator 49. The motor 36 is actuated to unwind the cable 38 such that the sleeve 43 is allowed to slide down the vertical support 33 until the slit 46 and the slits of the collimator plates 48, 49 are even with the bottom of the portion of the body of the patient 12 which is to be X-rayed. The motor 36 is then actuated to wind the cable 38 upon the reel 37 thereby drawing the housing 45 and attached structures upwardly along the length of the support 33. The X-ray source 47 is also actuated while the housing 45 is being drawn up the support 33.

X-rays from the X-ray source 47 pass out of the housing 45 only through the horizontal slit 46 formed therethrough. Further collimation of the X-ray beam is achieved by the plates 48, 49, the X-rays passing through the slits of the collimators 48, 49. The normal cone shape of the X-ray beam is reduced to a substantially horizontal beam having a very small vertical dimension as the beam passes through the patient and impinges upon the film 23 of the bucky 13.

The X-rays pass through the patient 12 after passing through the collimator plates 48, 49. The X-rays pass through the grid 16 of the bucky 13. The plates 17 are arranged to cut out secondary radiation emissions. The X-rays then strike the cassette 19, the film 23 being exposed in part by the X-rays and primarily by the somewhat phosphorescent screens 22, 24 activated by the passage of X-rays therethrough. The sheet 26 then absorbs the X-rays such that they do not travel further and thereby create a hazard.

The photocell detector structure 58 of the feedback mechanism 30 is carried at the end of the holder bar 52 upwardly along the housing 45. The shortest straight line between the X-ray source 47 and the photocell detector structure 58 is perpendicular to the plates 48, 49 and the grid 16 and cassette 19 of the bucky 13 and passes through the spine of the patient 12. The sheet 26 of the bucky 13 is made thinner or is absent along a vertical line which marks the path of the point of intersection of the shortest X-ray path with the sheet 26 while the housing 45 is traversing the length of the support 33. Some X-rays are thereby permitted to pass through the sheet 26 to the photocell detector structure 58. The X-rays pass through the aperture 60, the sheet 61 thereover screening out visible light, and are channelled through the baffles 62 directly toward the photocell 63. Additional shielding (not shown) is situated behind the structure 58 to stop the X-rays which were allowed to pass through the lead sheet 26 such that no hazard is created.

X-rays striking the somewhat phosphorescent coating of the photocell 63 allows current to flow along the conductor 64 leading from the photocell 63 to a detection circuit 65. The detection circuit 65 triggers the control circuit 39 interposed between the power supply 41 and the motor 36. The housing 45 is thereby moved upwardly along the support 33 at such a rate that the X-ray intensity detected by the photocell detector structure 58 never exceeds a given value. The value selected is the minimum intensity of X-rays required to expose the film 23. The greater the intensity of the X-rays, the greater the current flowing through the detection circuit 65. The circuit 65 may include standard transistor amplification stages, and the control circuit 39 may include a silicon rectifier sensitive to voltage and current changes in the detection circuit 65. Schematics of the control and detection circuits 39, 65 have not been included herein, well-known circuit structures for the aforementioned purposes being readily available.

Where the linear X-ray source 47' is used, the aforementioned procedure is followed. The X-ray beam travels through the focal line slit area 82, the slit 46 and the slits of the collimators 48, 49. The X-ray beam is again a horizontal one, the vertical spread being narrow as before. The X-ray beam passes through the patient 12 and causes the film 23 to be exposed. The X-ray beam also travels through the grid 83 such that horizontal dispersion of the X-rays is reduced. The plates 86 of the grid 16' are parallel because the X-rays are made to travel in a path perpendicular to the cassette 19. Additional vertical grids (not shown) may be associated with the housing 45 or collimators 48, 49 to augment the effect of the grid 83.

The X-rays are generated by the linear source 47' by impingement of electrons from the cathode 71 upon the rotating anode 74 at an angle of incidence of from 5°–30°. Rotation of the anode 74 is accomplished by the motor 79 through the magnetic coupling of the members 78, 81. The slow speed-up mechanism (not shown) of the motor 79 facilitates the initial rotation of the anode 74 by lengthening the time it takes for the motor 79 to come to full speed. Due to the housing 45 and plates 48, 49 (and 85 if used), the X-rays which pass through the patient 12 are those which have passed through the focal line slit area 82.

Where the linear source 47'' is used, the precise angle of incidence of the electrons upon the anode 74 is controlled within the range of from 5° to 30°. Manual operation of the circuitry (not shown) associated with the beam control mechanism 98 varies the strength of the charge upon the front and rear plates 99, 101. The angle of incidence at which the beam of electrons from the cathode structure 97 strike the anode 74 is thereby varied. The sweep plates 102, 103 are connected to an alternating current circuit (not hown) such that the beam of electrons from the cathode 97 scans back and forth along the length of the anode 74. The deflection electromagnets (not shown), when used instead of the plates 99, 101, 102, 103, operate similarly to direct a beam of electrons from the cathode structure 97, which beam has been concentrated by the focusing anode (not shown) and the annular centering electromagnet (not shown). Penumbral effects, which cause the image upon the film 23 to lack in sharpness somewhat, are reduced by making the angle of incidence of the electrons upon the anode 74 small and within a narrow range. The feedback mechanism 30 may be used with the X-ray sources 47, 47' or 47'', or a modified feedback mechanism 30' may be used. Where the modified mechanism 30' is used, the room wherein the X-raying is being undertaken is darkened. A preliminary adjustment is made to the control circuit 39 to correct for the body-build type of the patient. A given current from the detection circuit 65, which normally actuates the control circuit 39 to adjust tbe motor 79 to one particular speed, is thereby made to cause circuit 39 to adjust the motor 79 to a higher or lower speed as the patient is of lesser or greater body-build type, respectively, than average. The elongated light source 88 and the light detector 91 are carried upwardly with the housing 45. The photocell detector structures 58 (without the sheet 61) detect light from the source 88. The body of the patient 12 screens out varying amounts of light, which variations in intensity are carried by the detection circuit 65 to the control circuit 39. The speed with which the housing 45 moves along the support is thereby varied in direct proportion to the intensity of the light detected.

It can be seen that the X-ray apparatus of this invention reduces the exposure of patients 12 to the minimum amount of radiation required to take an X-ray photograph. Each area of the body of the patient 12 in the vertical dimension is exposed to no more than the minimum amount of radiation necessary to photograph that particular area. The taking of full spine and other X-rays of patients 12 is thereby made much safer for the patient 12 and those who operate X-ray equipment. Since the different areas of the body of the patient 12 are no longer exposed to the same amount of radiation, the screens 22, 24 may be uniformly of the high-speed type, thereby eliminating the need for a plurality of screens of different speeds for the cervical, thoracic and lumbar regions of the patient 12.

The total energy requirements for X-raying are substantially reduced due to the proximity of the patient 12 to the X-ray source 47, 47' or 47'' and due to the variation of the scanning speed of the X-ray apparatus 11. A beam of a constant, lower intensity may be used, the exposure of the film 23 being ensured by suitable variation of the scanning time of the apparatus 11 for each area of the body of the patient 12.

Vertical distortion problems are eliminated since the X-ray beam is substantially horizontal. Where spinal areas are being analyzed, horizontal distortion is unimportant because horizontal beam spread in the area of the spine is minimal. However, application of one of the embodiments of this invention 11 substantially eliminates the horizontal distortion also. The magnification-free X-ray films obtained greatly facilitate analysis of the condition of patients 12. Thus it can be seen that the objects of this invention 11 are attained. The invention 11 may also be applied to industrial usages where the taking of an X-ray film free of magnification can permit a more precise analysis of the object being filmed.

Although a preferred embodiment and alternate embodiment have been disclosed herein, it is to be remembered that various modifications and alternate constructions can be made thereto without departing from the full scope of the invention, as defined in the appended claims.

I claim:

1. An apparatus for X-raying, a bucky for full body X-raying having a grid and a film cassette disposed in parallel therein, the patient being disposed in front of the bucky near to the side of the bucky adjacent the grid, said apparatus for X-raying comprising:

elongated means for supporting, the patient being disposed between the bucky and said means for supporting, the patient and the bucky being disposed parallel to said means for support;

source means for providing X-rays, said source means being attached to said means for supporting perpendicular thereto and slidable along the length thereof, said source means being directed toward the patient whereby X-rays are made to pass through the patient into the bucky;

motor means attached to said means for supporting and to said source means, said motor means operable upon actuation to move said source means along the length of said means for supporting; and feedback means for detecting opaqueness of the body of the patient to X-rays, said feedback means being coupled to said motor means, said feedback means operating said motor means to move said source means along the length of said means for supporting at a rate inversely proportional to the opaqueness of the body of the patient to the X-rays.

2. An apparatus for X-raying as described in claim 1 and further wherein said feedback means extends to a position on the opposite side of the bucky from the patient, said feedback means detecting X-rays from said source means passing through the patient and the bucky, said feedback means operating said motor means to move said source means along the length of said means for supporting at a rate directly proportional to the intensity of the X-rays detected.

3. An apparatus for X-raying as described in claim 1 and further wherein said means for supporting includes at one end thereof pulleys attached thereto, said motor means including a cable extending therefrom, passing over said pulleys and attaching to said source means whereby actuation of said motor means moves said source means along the length of said means for supporting.

4. An apparatus for X-raying as described in claim 1 and further wherein said source means includes an X-ray tube source, a housing and at least one collimation structure, said X-ray tube source being disposed within said housing, said collimation structure being attached to said housing, said collimation structure and said housing having horizontally disposed slits formed therethrough, the X-rays from said source means passing through said slits to the patient and the bucky whereby images captured by the cassette have minimal vertical distortion, said collimation structure moving together with said housing and X-ray tube source along the length of said means for supporting.

5. An apparatus for X-raying as described in claim 4 and further wherein said X-ray tube source is horizontally disposed and includes an elongated, cylindrical tube, a cathode, an anode, and a motor, said cathode and said anode being disposed within said cylindrical tube parallel to the longitudinal axis thereof, said anode being rotatably mounted within said cylindrical tube, said motor being disposed external to said cylindrical tube and magnetically coupled to said anode to rotate said anode.

6. An apparatus for X-raying as described in claim 5 and further wherein said cylindrical tube has an elongated, slit-shaped focal line area parallel to said anode, the X-rays emitting from said anode passing through said focal line area, said X-ray tube having at least one X-ray opaque vertical grid affixed thereto perpendicular to said focal line area and to the longitudinal axis of said X-ray tube.

7. An apparatus for X-raying as described in claim 2 and further wherein said feedback means includes a holder bar and a photocell detector means, said holder bar being attached to said source means and being cantilevered therefrom, said holder bar having a terminating end disposed on the opposite side of the bucky from the patient, said photocell detector means being supported at said terminating end and being coupled to said motor means, said photocell detector means detecting X-rays passing through the patient and the bucky and adjusting the rate of speed of said motor means directly with the intensity of the X-rays detected.

8. An apparatus for X-raying as described in claim 7 and further wherein said photocell detector means includes a cylindrical clarifier member, a plurality of annular members, and a photocell, said cylindrical clarifier member having an open end, said annular members being uniformly spaced and attached to the inside of said cylindrical clarifier member perpendicular to the longitudinal axis thereof, said photocell being attached to said cylindical clarifier member opposite said open end and being coupled to said motor means, the X-rays passing through said open end and said annular members to strike said photocell, said open end having a cover thereover, said cover being opaque to visible light.

9. An apparatus for X-raying as described in claim 1 and further wherein said feedback means includes an elongated light source and a light receptor member, said light source and said light receptor being disposed horizontally, on opposite sides of the patient, and normal to the bucky and said means for supporting, said light receptor detecting light from said light source, the amount of light detected being directly proportional to the thickness of the patient, said light receptor being coupled to said motor means to operate said motor means at a rate directly proportional to the amount of light detected.

10. An apparatus for X-raying as described in claim 9 and further wherein said light receptor includes a plurality of photocell detector means, said photocell detector means being uniformly spaced, oriented normal to the longitudinal axis of said light receptor and directed toward said light source, each photocell detector means including a cylindrical clarifier member, a plurality of annular members, and a photocell, said cylindrical clarifier member having an open end, said annular members being uniformly spaced and attached to the inside of said cylindrical clarifier member perpendicular to the longitudinal axis thereof, said photocell being attached to said cylindrical clarifier member opposite said open end and being coupled to said motor means, the light passing through said open end and said annular members to strike said photocell.

11. An apparatus for X-raying as described in claim 10 and further wherein said elongated light source has a vertical grid affixed thereto and disposed between said elongated light source and said light receptor.

12. A method of body X-raying comprising:
positioning a bucky, said bucky having a grid and a cassette disposed in parallel, said cassette containing film;
positioning the patient with respect to the bucky such that the body area to be X-rayed of the patient is disposed in front of said bucky;
disposing an X-ray source such that the body area to be X-rayed is between said X-ray source and said bucky;
actuating said X-ray source to direct an X-ray beam toward the body area and therethrough to cause an image to be formed upon said film;
collimating said X-ray beam into an elongated, thin beam;
moving said X-ray source with respect to the body area being X-rayed and in a direction which is normal to the plane defined by said elongated, thin beam;
simultaneously detecting the opaqueness to X-rays of the portion of the body area being struck by said elongated, thin beam;
instantaneously altering the rate at which said X-ray source is being moved with respect to the body area being X-rayed, the rate being altered in inverse proportion to the opaqueness detected, whereby the duration of exposure to X-rays of the body area being X-rayed is minimized, and vertical distortion of the image captured upon said film is reduced.

* * * * *